United States Patent

Schroeder

[11] 4,090,018
[45] May 16, 1978

[54] WHITENERS, THEIR PREPARATION AND USE

[75] Inventor: Josef Schroeder, Cologne, Germany

[73] Assignee: Bayer Aktiengesellschaft, Leverkusen-Bayerwerk, Germany

[21] Appl. No.: 759,007

[22] Filed: Jan. 13, 1977

[30] Foreign Application Priority Data

Jan. 16, 1976 Germany .............................. 2601469

[51] Int. Cl.² ............................................ C07D 55/04
[52] U.S. Cl. ................................ 542/458; 252/301.22
[58] Field of Search ................... 260/240 D; 542/458

[56] References Cited

U.S. PATENT DOCUMENTS 3,758,460  9/1973  Schroeder et al. .............. 260/240 D

FOREIGN PATENT DOCUMENTS 1,560,056  2/1969  France.

OTHER PUBLICATIONS

Imahori et al., Chemical Abstracts 81, (1974), #51149k.
Siegrist et al., Helv. Chim. Acta 55, (1972), pp. 2300, 2301, 2307, 2309, 2310.

Primary Examiner—Arthur P. Demers
Attorney, Agent, or Firm—Plumley & Tyner

[57] ABSTRACT

2-Styrylbenztriazoles of the formula

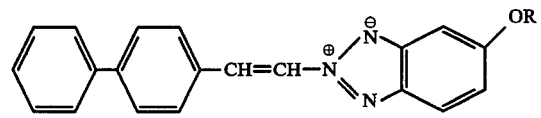

in which R denotes $C_1$–$C_4$-alkyl, benzyl or $C_1$–$C_4$-alkoxyethyl are suitable for whitening organic materials.

1 Claim, No Drawings

WHITENERS, THEIR PREPARATION AND USE

The invention relates to 2-styrylbenztriazoles of the formula

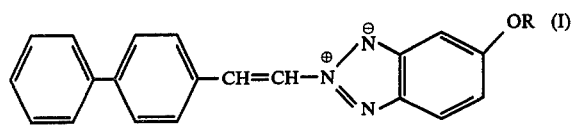

wherein

R denotes $C_1$–$C_4$-alkyl, benzyl or $C_1$–$C_4$-alkoxyethyl, and to their preparation and use as whiteners.

The new compounds of the formula I are obtained when the corresponding benztriazolyl-2-acetic acids of the formula

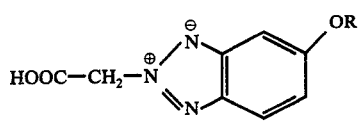

wherein

R has the abovementioned meaning, are reacted with p-diphenylaldehyde in the presence of suitable condensing agents.

The condensation reaction can be carried out in the absence or in the presence of an organic solvent. However, the reaction in solvents is preferred.

Examples of suitable solvents are dimethylformamide, xylene, chlorobenzene or o-dichlorobenzene.

Suitable catalysts for the condensation reaction are secondary aliphatic amines, such as diethylamine, morpholine or piperidine.

The reaction temperatures can be varied within a relatively wide range; in general, the reaction is carried out between 100° and 200° C, preferably between 130° and 170° C.

p-Diphenylaldehyde is known.

The 5-alkoxybenztriazolyl-2-acetic acids are obtained by reductive cyclisation of o-nitroazo dyestuffs of the formula

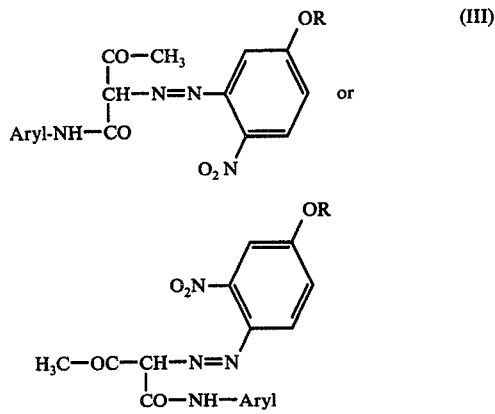

wherein

R has the meaning designated above, and subsequent saponification of the acetoacetic acid arylide component, or by alkylation of the corresponding benztriazoles with chloroacetic acid. In the case of the last-mentioned process, mixtures of benztriazole-N-acetic acids are obtained and these can be employed in the condensation reaction as such or after they have been separated into the individual components.

Particularly suitable benztriazolylacetic acids are 5-methoxy-benztriazolyl-2-acetic acid, 5-ethoxybenztriazolyl-2-acetic acid, 5-benzyloxybenztriazolyl-2-acetic acid and 5-(2-methoxyethoxy)-benztriazolyl-2-acetic acid and 5-butoxybenzotriazole-acetic acid.

The new compounds of the formula I are suitable for whitening very diverse organic materials and are distinguished by very good fastness to light and stability to chemical agents, for example bleaching agents. The new compounds are particularly suitable for whitening synthetic organic fibre materials based on polyester or polyamide, for example those consisting of polyethylene glycol terephthalate and poly-ε-caprolactam, and plastics, such as plasticised PVC, polyethylene and polypropylene, as well as latices of acrylic esters, polyvinyl ester and polystyrenes, can be brightened readily.

The new compounds of the formula I display advantages, in respect of the whiteness and the lower dyeing temperature, over comparable compounds, especially on textured polyester fibres.

Brightening of the textile materials is preferably effected in an aqueous medium, from solution or dispersion. Dispersing agents, such as soaps, polyglycol ethers of fatty alcohols, fatty amines or alkylphenols, cellulose sulphite waste liquors or condensation products of optionally alkylated naphthalenesulphonic acids and formaldehyde, can optionally be added. Whitening can be effected from a neutral, weakly alkaline or acid bath. The whiteners can also be applied from solutions in organic solvents.

The amount of the new whiteners to be used according to the invention, relative to the material to be whitened, can vary within wide limits. In general, amounts of between 0.01 and 0.2 percent by weight are used.

EXAMPLE 1

70 g of 5-methoxybenzotriazole are dissolved in 200 ml of ethanol and this solution is added to a solution of 22 g of powdered sodium hydroxide in 250 ml of ethanol. The mixture is stirred under reflux for 1 hour and 63 g of sodium chloroacetate are then added. After 5 hours under reflux, the thick suspension is brought into solution with 1.5 l of water and the solution is then acidified. A mixture (92 g) of 5- and 6-methoxy-benzotriazole-N-acetic acids is obtained and is further processed in the crude form.

19.1 g of the mixture are stirred with 18.2 g of p-diphenylaldehyde in 50 ml of dimethylformamide, in the presence of 5 ml of piperidine, under reflux for 5 hours. After cooling, 13 g of golden yellow flakes are obtained and, on recrystallisation from methylglycol, these give 10.5 g of the product, which has a melting point of 176° C. The product has the formula

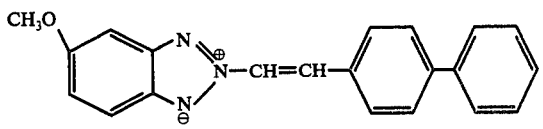

The compound of the formula

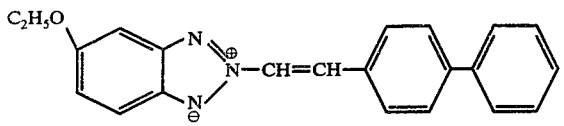

which has a melting point of 142° C (benzine), was obtained in an analogous manner.

EXAMPLE 2

168 g of 2-nitro-4-methoxyaniline are suspended in 850 ml of 50% strength acetic acid and 100 ml of concentrated hydrochloric acid are added. A diazotisation reaction is carried out at 0° to 5° C with 69 g of $NaNO_2$ in 150 ml of $H_2O$ and during this reaction the suspension goes into solution. A solution of 177 g of acetoacetanilide in 500 ml of ethanol and 122 ml of concentrated sodium hydroxide solution is added to this solution. A thick yellow suspension of 2-[2-nitro-4-methoxyphenylazo]-3-ketobutyric acid anilide forms. The product is filtered off, washed with a large amount of water and dried; the yield is 354 g and the melting point is 222° C.

2-[2-Nitro-4-n-butoxy-phenylazo]-3-ketobutyric acid anilide, which has a melting point of 150° C, 2-]2-nitro-4-benzyloxyphenylazo]-3-ketobutyric acid anilide, which has a melting point of 190° to 6° C, and 2-[2-nitro-4-(β-methoxyethoxy)-phenylazo]-3-ketobutyric acid anilide, which has a melting point of 183° to 5° C, were prepared analogously.

35.6 g of 2-[2-nitro-4-methoxyphenylazo]-3-ketobutyric acid anilide in a mixture of 100 ml of pyridine, 250 ml of methylglycol and 25 ml of water are heated to the boil. About 100 g of zinc are introduced in small portions in the course of 1 hour. During this period, a colourless solution forms. The zinc is filtered off hot and the filtrate is diluted with water. 5-Methoxybenzotriazole-2-acetic acid anilide precipitates as a white mass of crystals. After recrystallisation from methylglycol, the product melts at 217° to 9° C.

5-n-Butoxy-benzotriazole-2-acetic acid anilide, which has a melting point of 165° C (DMF), 5-benzyloxy-benzotriazole-2-acetic acid anilide, which has a melting point of 191° – 2° C (methylglycol), and 5-(β-methoxyethoxybenzotriazole-2-acetic acid anilide, which has a melting point of 183° – 5° C (methylglycol), were obtained analogously.

17 g of 5-methoxybenzotriazole-2-acetic acid anilide are saponified on ethanol with 60 ml of 20% strength NaOH sodium hydroxide solution. After diluting the reaction mixture with water, separating off the insoluble matter and acidifying the solution, 9.4 g of 5-methoxybenzotriazole-2-acetic acid, which has a melting point of 190° to 3° C, are obtained. 5-n-Butoxy-benzotriazole-2-acetic acid, 5-benzyloxy-benzotriazole-2-acetic acid and 5-(β-methoxyethoxy)-benzotriazole-2 -acetic acid are obtained analogously.

21 g of 5-methoxybenzotriazole-2-acetic acid, 20 g of 4-formyl-biphenyl and 5 ml of piperidine are melted at 165° to 175° C for 10 hours. 50 ml of dimethylformamide are then added and the product is allowed to crystallise. 20 g of 5-methoxy-2-[(p-phenyl)-styryl]-benzotriazole are obtained and after recrystallisation from methylglycol this melts at 176° C.

5-n-Butoxy-2-[(p-phenyl)-styryl]-benzotriazole, which has a melting point of 118° to 20° C, 5-benzyloxy-2-[(p-phenyl)-styryl]-benzotriazole, which has a melting point of 197° to 9° C, and 5-(β-methoxyethoxy)-2-[(p-phenyl)-styryl]-benzotriazole, which has a melting point of 117° to 20° C, were obtained analogously.

EXAMPLE 3

(a) Using a liquor ratio of 1:40, filaments of polyethylene terephthalate are treated at the boil for 1 hour with 0.1%, relative to the material to be dyed, of 5-methoxy-2-(p-phenyl)-styrylbenzotriazole, in the presence of the customary dyeing auxiliaries. The polyester filaments display a very brilliant, neutral whitening with good fastness to light.

(b) A textured fabric made of polyethylene terephthalate is padded with a dye liquor which contains 2 g of 5-methoxy-2-[(p-phenyl)-styryl]-benzotriazole per liter, squeezed off to an increase in weight of 80% and heated to 160° C for 20 seconds. A very well brightened fabric, which has good fastness to light, is obtained.

I claim:
1. 2-Styrylbenztriazoles of the formula

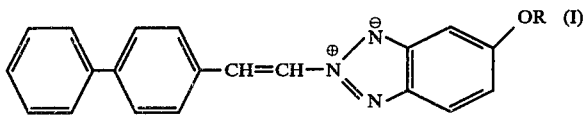

wherein
R denotes $C_1$–$C_4$-alkyl, benzyl or $C_1$–$C_4$-alkoxyethyl.

* * * * *